United States Patent [19]

Whatley et al.

[11] Patent Number: 5,286,108

[45] Date of Patent: Feb. 15, 1994

[54] FIXTURE FOR PERFORMING TENSILE TESTS AT EXTREMELY HIGH TEMPERATURE

[75] Inventors: Walter J. Whatley, San Diego; Gregory M. Duchnak, Vista, both of Calif.

[73] Assignee: Hughes Missile Systems Company, Los Angeles, Calif.

[21] Appl. No.: 891,515

[22] Filed: Jun. 1, 1992

[51] Int. Cl.⁵ .............................................. G01N 3/18
[52] U.S. Cl. ...................................... 374/49; 73/826
[58] Field of Search ................... 374/49, 50; 73/8, 826

[56] References Cited

U.S. PATENT DOCUMENTS

| 2,748,597 | 6/1956 | Kooistra | 374/49 |
| 2,763,149 | 9/1956 | Long et al. | 374/49 |
| 3,176,499 | 4/1965 | Sikora | 374/50 |
| 3,324,713 | 6/1967 | Krock et al. | 374/49 X |
| 3,558,281 | 1/1971 | Dyer | 374/49 X |

Primary Examiner—Daniel M. Yasich
Attorney, Agent, or Firm—Randall M. Heald; Charles D. Brown; Wanda K. Denson-Low

[57] ABSTRACT

A fixture for performing tensile tests on advanced materials at extremely high temperatures (greater than 2500 degrees fahrenheit). The fixture allows gripping a specimen without introducing thermal gradient in the specimen. It incorporates a self aligning feature while avoiding thermal stress problems inherent in using different materials at elevated temperatures.

11 Claims, 1 Drawing Sheet

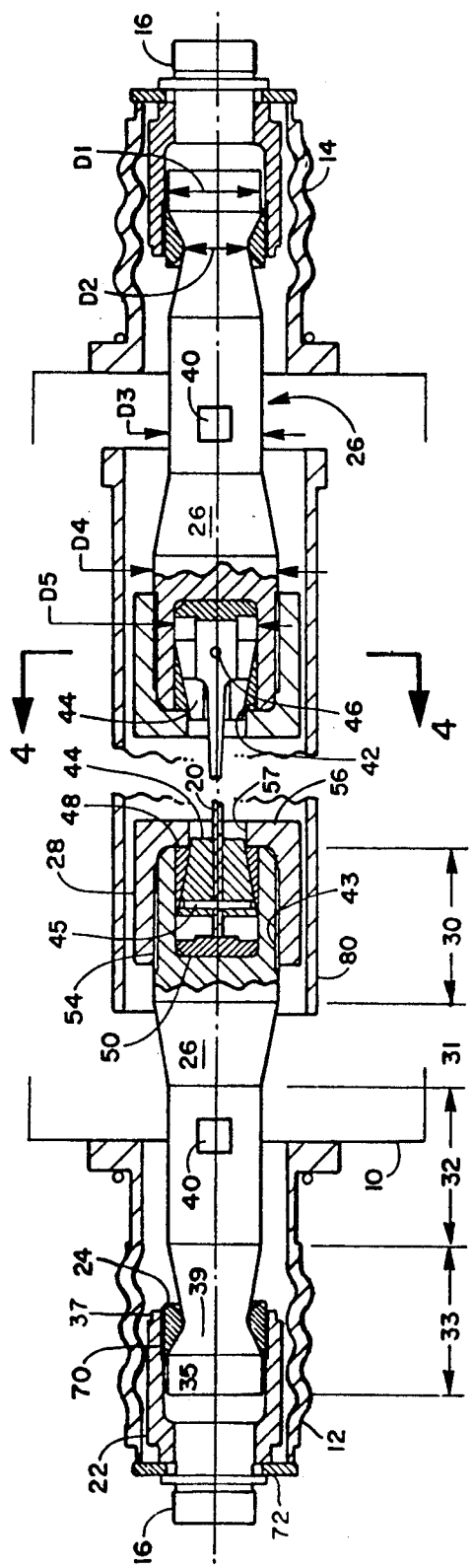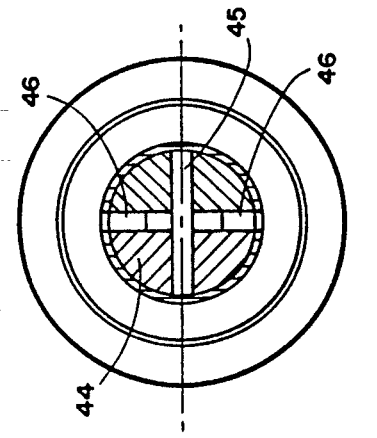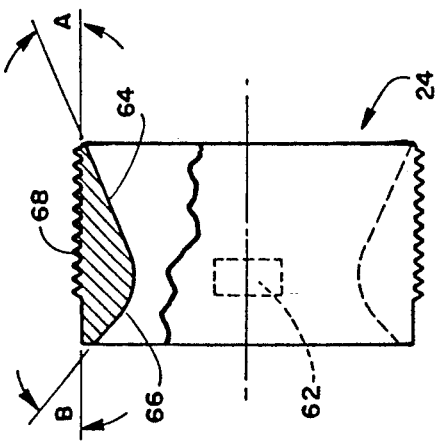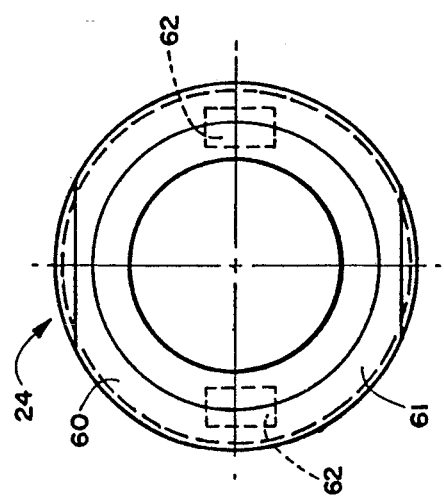

FIXTURE FOR PERFORMING TENSILE TESTS AT EXTREMELY HIGH TEMPERATURE

BACKGROUND OF THE INVENTION

This invention relates in general to a fixture for performing and more specifically where the tensile tests are performed at extremely high temperatures (greater than 2500 degrees Fahrenheit).

Performing tensile tests on advanced materials at extremely high temperatures poses many problems. Among the most critical are specimen alignment and gripping.

Elevated temperature testing is performed at several locations. Among these are Southern Research Institute, IITRI and EMTL. All of these institutions have unique approaches to high temperature testing.

Current state-of-the-art elevated temperature tensile testing uses hot grips. At elevated temperatures, transferring the load from the hot grips to the load train is problematic. The extremely high temperatures require the use of material such as graphite or silicon carbide. These materials have coefficients of expansion which are much lower than the metals used in the load train. This creates the possibility of fixture damage, or misalignment due to the differential growth at test temperature.

It is an object of the invention to provide a novel fixture for performing tensile tests at extremely high temperatures that incorporates a self aligning feature while avoiding thermal stress problems inherent in using different materials at elevated temperatures.

It is also an object of the invention to provide a novel fixture for performing tensile tests at extremely high temperatures that allows gripping a specimen without introducing thermal gradients in the specimen.

SUMMARY OF THE INVENTION

One of the key elements of the invention is the method used to transfer a load between the fixture and the load train. Mating conical bearing surfaces on the split collet and the collet attaching portion of the pull rod are used to make this attachment. This allows for self alignment. More importantly it provides a thermal stress free attachment between the test fixture and the load train of the test machine. As the two components are heated, each expands at its own rate. This has the effect of changing the diameter of the two cones. Since the angle of the two cones is unchanged, the result of the differential growth is a small displacement along the axis of the fixture.

The pull rod of the fixture is preferably made of graphite material. One end of the pull rod has conical bearing surfaces that engage the conical bearing surfaces of the split collet. The outer cylindrical surface of the split collet assembly is externally threaded so that it may screw into the internal threads on one end of a tubular high temperature coupling which is in turn connected to the load train of a test machine.

The high temperature split collet assembly and the threaded high temperature coupling retaining ring are fabricated from the same high temperature alloy, preferably Inconel.

A second major improvement in the design of the fixture is the method used to retain the gripping mechanism for the test specimen. The end of the pull rod opposite from the conical bearing surfaces is externally threaded and a retaining cup is internally threaded so that they screw together. By moving the threads to the outside of the pull rod, the bearing area has been greatly increased. This results in a large reduction of the stresses in the threads.

DESCRIPTION OF THE FIGURES OF THE DRAWING

FIG. 1 is a side elevation view of the novel fixture for performing tensile tests at extremely high temperatures illustrating some portions in cross section and other structure in a broken away view;

FIG. 2 is a front elevation view of the split collet assembly;

FIG. 3 is a side elevation view of the split collet assembly with portions broken away;

FIG. 4 is a cross sectional view taken along lines 4—4 of FIG. 1; and

FIG. 5 is an end elevation view of the retaining collar.

DESCRIPTION OF THE PREFERRED EMBODIMENT

The fixture for performing tensile tests at extremely high temperature will now be described by referring to FIGS. 1-5 of the drawings. The fixture is mounted inside a tubular housing 10 that has bellows 12 and 14 connected to its opposite ends. The load train connections 16 pass through the outer end of the respective bellows 12 and 14 and are connected to the fixture in the manner to be later described.

The fixture is comprised of two identical sets of assembled structure that are connected to the opposite ends of an elongated test specimen 20. For ease of description and clarity, only one of the structures attached to an end of the test specimen will be described. There are four major components that are part of the test fixture that is secured to one end of the test specimen. These are high temperature coupling or retaining ring 22, split collet assembly 24, pull rod 26 and retaining collar or cup 28.

Pull rod 26 is the major component and it will now be described. It has a test specimen receiving portion 30, an intermediate portion 31, a central portion 32, and a collet attaching portion 33.

Collet attaching portion 33 has a cylindrical section 35, a first cone shaped section 37, and a second cone shaped section 39. Cylindrical section 35 has an outer diameter D1. Second cone shaped section 39 has a diameter D2 at its narrowest point and a diameter D1 at its widest point. First cone shaped section 37 has a diameter D3 at its widest point and a diameter D2 at its narrowest point. Second cone shaped section 39 has a slope of approximately 63.5 degrees. First cone shape section 37 has a slope of between 73 to 83 degrees.

Central portion 32 has an outer diameter D3 and a pair of diametrically opposed flat surface areas 40.

Test specimen portion 30 has an outer diameter D4. It also has a recessed chamber 42 for securing one end of a test specimen. External threads 43 are formed on the outer surface of test specimen receiving portion 30.

The manner in which the end of test specimen 20 is captured within recess chamber 42 will now be discussed. Grip plate 44 is secured thereto perpendicular intersecting pins 45 and 46. Conical retainer sleeve 48 wedges against grip plate 44. A spacer 50 is positioned at the rear of recess chamber 42. Retaining collar 28 has internal threads 54 that engage external threads 43 of test specimen receiving portion 30. Retaining collar 28 has an end wall 56 that bears against conical retainer 48. It also has an aperture 57 which allows the end of the specimen to pass therethrough.

Split collet assembly 24 is formed from two split halves 60 and 61 that are connected together by pins 62. Split collet assembly 24 has a first cone shaped surface 64 and a second cone shaped surface 66. The angle of cone shaped surface 64 mates with the second cone shaped section 39 of the pull rod 26. Split collet assembly 24 has external threads 68 that mate with internal threads 70 of high temperature coupling/retaining ring 22. Retaining ring 22 also has internal threads 72 that thread onto the end of the load train connection 16.

A heating element 80 surrounds test specimen 20 and part of the fixture structure holding the heating element.

What is claimed is:

1. A fixture for performing tensile texts at extremely high temperature comprising:
   a pair of elongated pull rods, each of said elongated pull rods having a first end and a second end, each of said pull rods having a test specimen receiving portion at said first end and a collet attachment portion at said second end;
   means for detachably securing one end of a test specimen to the first end of each of said pull rods;
   said collet attaching portion having an outer surface having a fist cone shaped section and a second cone shaped section, said second cone shaped section having its largest diameter D1 closest to the second end of its said pull rod, said second cone shaped section having its smallest diameter D2 also forming the smallest diameter for said first cone shaped section whose diameter is D3;
   an annular collet for each of the pull rods, the collet having an outer surface and an inner surface, the inner surface of said collet having a first cone shaped surface that mates with the second cone shaped section, wherein said collet is formed from two longitudinally split halves having means for detachably securing the two halves together in an assembled annular structure; and
   a tubular first retaining ring for each of the pull rods and means on the outer surface of said annular shaped collet for detachably securing it to the inner surface of said first retaining ring.

2. A fixture for performing tensile tests at extremely high temperatures as recited in claim 1 wherein said tubular retaining ring has means on its inner surface for detachably securing it to one end of the load train of a test machine.

3. A fixture for performing tensile tests at extremely high temperatures as recited in claim 1 wherein said collet attaching portion has a cylindrical section having a diameter D1 adjacent the second end of said pull rod.

4. A fixture for performing tensile tests at extremely high temperatures as recited in claim 1 wherein said means for detachably securing one end of a test specimen to the first end of a pull rod comprises a recess chamber in said first end for detachably receiving one end of a test specimen, said recess chamber also removably receives structure for gripping a test specimen.

5. A fixture for performing tensile tests at extremely high temperatures as recited in claim 4 further comprising a retaining cup and means for detachably securing it over the first end of said pull rod.

6. A fixture for performing tensile tests at extremely high temperatures as recited in claim 1, and further comprising a tubular heating element surrounding at least the test specimen.

7. A fixture for performing tensile tests at extremely high temperatures as recited in claim 1 wherein each of said elongated pull rods has the following structure in sequence from its first end to its second end: a test specimen receiving portion, an intermediate portion, a central portion and a collet attaching portion.

8. A fixture for performing tensile tests at extremely high temperatures as recited in claim 7 wherein said central portion has a diameter D3 and said test specimen receiving portion has a diameter D4 and D4 is greater than D3.

9. A fixture for performing tensile texts at extremely high temperatures comprising:
   a pair of elongated pull rods, each of said elongated pull rods having a first end and a second end, each of said pull rods having a test specimen receiving portion at said first end and a collet attachment portion at said second end;
   means for detachably securing one end of a test specimen to the first end of each of said pull rods, the means for detachably securing comprising a recess chamber in said first end for detachably receiving one end of a test specimen and for receiving structure for gripping a test specimen;
   said collet attaching portion having an outer surface having a first cone shaped section and a second cone shaped section, said second cone shaped section having its largest diameter D1 closest to the second end of its said pull rod, said second cone shaped section having its smallest diameter D2 also forming the smallest diameter for said first cone shaped section whose diameter is D3;
   an annular collet for each of the pull rods, the collet having an outer surface and an inner surface, the inner surface of said collet having a first cone shaped surface that mates with the second cone shaped section; and
   a tubular first retaining ring for each of the pull rods and means on the outer surface of said annular shaped collet for detachably securing it to the inner surface of said first retaining ring.

10. A fixture for performing tensile tests at extremely high temperatures as recited in claim 9 further comprising a retaining cup and means for detachably securing it over the first end of said pull rod.

11. A fixture for performing tensile tests at extremely high temperatures as recited in claim 9, and further comprising a tubular heating element surrounding at least the test specimen.

* * * * *